(12) United States Patent
Yamaguchi et al.

(10) Patent No.: US 7,473,895 B2
(45) Date of Patent: Jan. 6, 2009

(54) TWO-DIMENSIONAL IMAGE DETECTOR, AND RADIOGRAPHIC APPARATUS USING THE TWO-DIMENSIONAL IMAGE DETECTOR

(75) Inventors: Narumi Yamaguchi, Kyoto (JP); Toshinori Yoshimuta, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 22 days.

(21) Appl. No.: 11/791,173

(22) PCT Filed: Nov. 29, 2005

(86) PCT No.: PCT/JP2005/021911

§ 371 (c)(1), (2), (4) Date: May 21, 2007

(87) PCT Pub. No.: WO2006/073031

PCT Pub. Date: Jul. 13, 2006

(65) Prior Publication Data

US 2007/0295906 A1 Dec. 27, 2007

(30) Foreign Application Priority Data

Jan. 7, 2005 (JP) .............................. 2005-001976

(51) Int. Cl.
*G01J 1/00* (2006.01)

(52) U.S. Cl. .................................................. 250/336.1

(58) Field of Classification Search ................. 250/580, 250/336.1, 370.01, 370.08, 370.09; 378/98.8
See application file for complete search history.

(56) References Cited

U.S. PATENT DOCUMENTS

2004/0227096 A1* 11/2004 Yagi ...................... 250/370.09

FOREIGN PATENT DOCUMENTS

| JP | 2001-346788 A | 12/2001 |
|---|---|---|
| JP | 2002-009268 | 1/2002 |
| JP | 2002-214352 A | 7/2002 |

\* cited by examiner

*Primary Examiner*—David P Porta
*Assistant Examiner*—Kiho Kim
(74) *Attorney, Agent, or Firm*—Cheng Law Group PLLC

(57) ABSTRACT

The present invention is directed to an image detector having a housing of protrusive sectional shape. A difference in thickness between a central portion and peripheral portions of the housing is made shorter than the length of rubber cushions. A plurality of rubber cushions are attached to two rectangular bottoms of the peripheral portions made thinner than the central portion. Through these rubber cushions, the image detector is fixed to an image detector holder. As a result, the present invention reduces an inconvenience that, when an image detector is fixed to an image detector holder through rubber cushions, the thickness of the image detector including the rubber cushions increases by an amount corresponding to the height of the rubber cushions.

10 Claims, 4 Drawing Sheets

TWO-DIMENSIONAL IMAGE DETECTOR, AND RADIOGRAPHIC APPARATUS USING THE TWO-DIMENSIONAL IMAGE DETECTOR

TECHNICAL FIELD

This invention relates to a two-dimensional image detector that can detect images of radiation or light, and a radiographic apparatus using the two-dimensional image detector.

BACKGROUND ART

Two-dimensional image detectors include a type having a planar and relatively large light-receiving surface, such as an X-ray flat panel type detector, for example, that receives X rays transmitted through a human body, by means of numerous X-ray detecting elements arranged in a matrix form, and converts image information on an X-ray transmitted image of the human body into electric signals (see Patent Document 1, for example).

Generally, such an image detector has, arranged in a housing, a planar image detecting substrate with a light receiving section having numerous radiation or light detecting elements arranged in a matrix form, a peripheral circuit board of the image detecting substrate, such as a data read control board for controlling timing of reading image data detected by the image detecting substrate, a power source-related board for supplying power to the image detecting substrate and the detector's peripheral circuit board, a cooling mechanism for heat-generating portions of each board, and connectors of signal and power wires connected from outside the image detector.

Usually, such an image detector is used as an image detecting unit of an image collecting and processing apparatus, and includes portions in its interior that handle image data signals of low strength. Therefore, noise can occur with the image data when the image detector undergoes mechanical vibration or shock. In order to reduce this noise, the image detector may be mounted on an image detector holder of the image collecting and processing apparatus through vibration proof members such as rubber cushions.

FIGS. 3 (A) and (B) show a plan view and a front view of an image detector 1. FIGS. 3 (A) and (B) also show schematically a state where the image detector 1 is mounted on an image detector holder 4 through rubber cushions 3.

As noted above, the image detector 1 includes portions in its interior that handle image data signals of low strength, and therefore noise will occur with image data as a result of mechanical vibration or shock. Thus, the image detector 1 is mounted on the image detector holder 4 of an image collecting and processing apparatus (not shown in FIG. 1) through four rubber cushions 3.

[Patent Document 1] Unexamined Patent Publication No. 2002-9268

DISCLOSURE OF THE INVENTION

[Problems to be Solved by the Invention]

With the image collecting and processing apparatus using such an image detector as an image detecting unit, the distance between a light source and the image detector usually is restricted, for example, by the size of a room where it is installed, and in many cases an object placed in between to be radiographed has a certain thickness. It is therefore desirable that the image detector is made as thin as possible.

However, since noise occurs with image data when the image detector 1 undergoes mechanical vibration or shock as noted above, the image detector 1 is mounted on the image detector holder 4 through vibration proof members such as the rubber cushions 3 attached to the four corners of the bottom of a housing 2 as shown in FIGS. 3 (A) and (B). As a result, the image detector 1 is raised by the rubber cushions 3 by an amount corresponding to their height. Compared with the case where there are no rubber cushions 3, the same inconvenience is caused as when the thickness of the image detector 1 is increased by an amount corresponding to the height of the rubber cushions 3.

The rubber cushions 3 used in such a case, as shown in the plan view of FIG. 4 (A) and the sectional view of FIG. 4 (B), for example, have a structure in which a rubber material 3E is held between an upper fixture 3B having a mounting screw hole 3A, and a lower fixture 3D having a mounting screw rod 3C. Thus, after the rubber cushions 3 are fixed with the mounting screw rods 3C screwed into screw holes formed in the image detector holder 4 shown in FIG. 3 (B), the image detector 1 is screwed to the mounting screw holes 3A of the rubber cushions 3 shown in FIG. 4 (B). Then, the rotation of the screws is transmitted to the upper fixtures 3B by friction, whereby the upper fixtures 3B also rotate to a certain extent. Since the lower fixtures 3D are already fixed to the image detector holder 4, the rubber materials 3E pinched between the upper fixtures 3B and lower fixtures 3D are fixed in a twisted state. This leads to shortening of the life of the rubber materials 3E, and deterioration in dampening property of the rubber cushions 3.

In view of the above-noted situation, an object of this invention is to provide a two-dimensional image detector that can be mounted at a height hardly influenced by a height of rubber cushions in a case where the image detector is mounted on an image detector holder through vibration proof members such as the rubber cushions. Another object is to provide a two-dimensional image detector free from shortening of the life of rubber cushions and, moreover, from deterioration in their damping characteristic when similarly mounted on an image detector holder.

[Means for Solving the Problem]

In order to fulfill the above objects, this invention provides a two-dimensional image detector comprising, mounted in a housing, a planar image detecting substrate with a light receiving section having radiation or light detecting elements arranged in a matrix form, and parts necessary for outputting image information detected by the image detecting substrate to an exterior of the housing, characterized in that stepped portions are formed over an entire circumference or in a plurality of locations peripherally of a radiation or light non-incidence surface of the housing for reducing a thickness of the housing and attaching vibration proof members for holding said housing.

Where rubber cushions are used as the above vibration proof members, the detector is characterized in that each of the rubber cushions includes a rubber material held between a pair of fixtures having mounting screws, at least one of said pair of fixtures having at least a set of two surfaces perpendicular to a mounting surface and parallel to each other.

[Effects of the Invention]

With this invention, when the image detector is attached to the image detector holder through the vibration proof members, it is possible to reduce an extent of the thickness of the image detector including the vibration proof members becoming thicker with attachment of the vibration proof members. This is effective particularly where the distance of a light source and the image detector is restricted, and an object placed therebetween has a large thickness.

With this invention, when the image detector is attached to the image detector holder through rubber cushions, screws can be turned while holding, with a tool such as a spanner, for example, two surfaces perpendicular to a mounting surface and parallel to each other, of fixtures of the rubber cushions. This can prevent twisting of the rubber material when the image detector is fixed on the rubber cushions. As a result, it is possible to prevent shortening of the life of the rubber cushions and a reduction of their damping effect

DESCRIPTION OF REFERENCE

Figure 1:
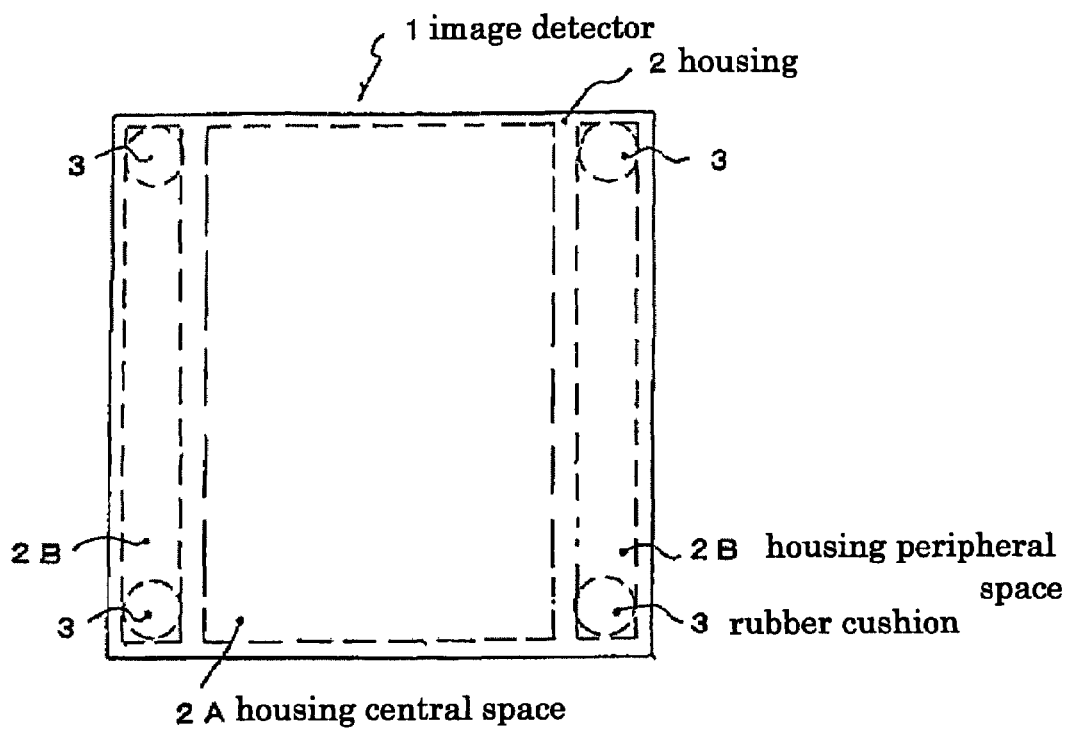
FIG. 1 Views schematically showing a housing configuration of an image detector in an embodiment, and a state of the image detector mounted on an image detector holder using rubber cushions.
Figure 1:
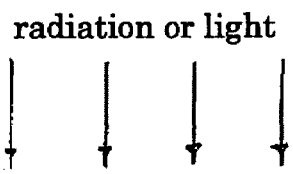
Figure 1:
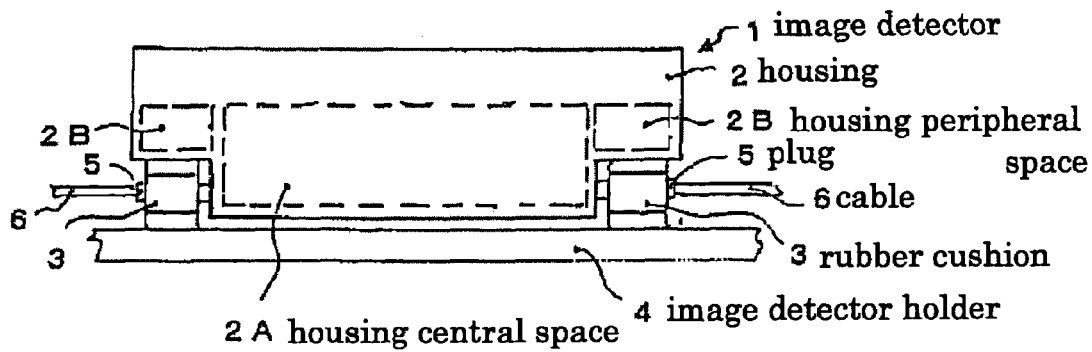

1: image detector
2: housing
2A: housing central space
2B: housing peripheral spaces
3: rubber cushions
3A: mounting screw holes
3B: upper fixtures
3C: mounting screw rods
3D: lower fixtures
3E: rubber materials
3F: upper fixture cutout portions
3G: lower fixture cutout portions
4: image detector holder
5: plugs
6: cables

BEST MODE FOR CARRYING OUT THE INVENTION

Figure 2:
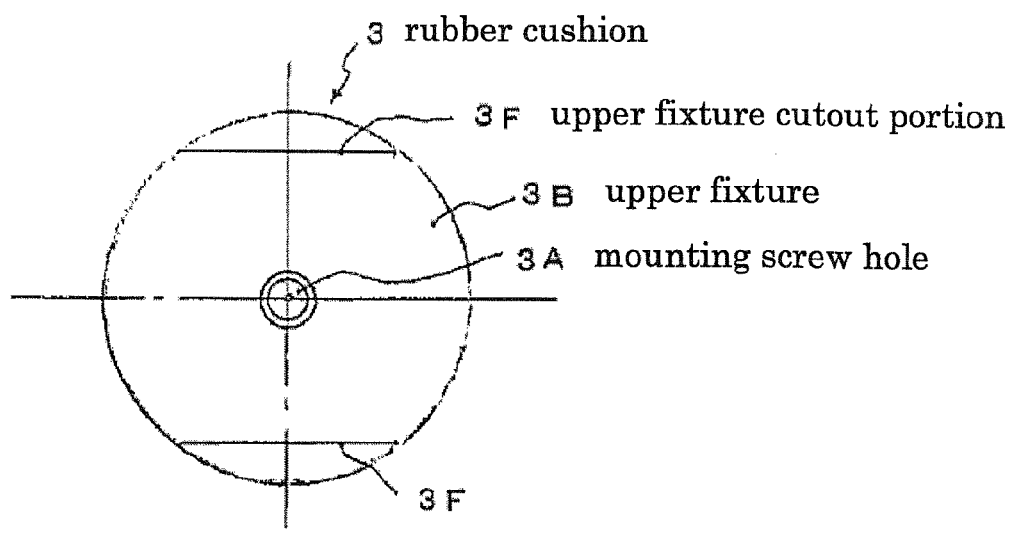
FIG. 2 Views showing a construction and configuration of a rubber cushion used in the embodiment.
Figure 2:
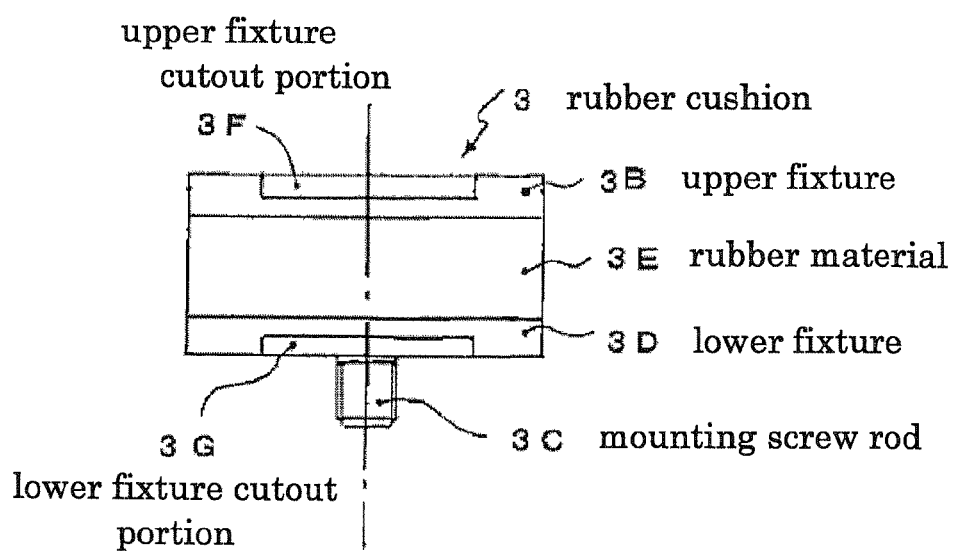

An embodiment of this invention will be described hereinafter using FIGS. 1 and 2. FIGS. 1 (A) and (B) are a plan view and a front view of an image detector to be described in the embodiment. FIGS. 1 (A) and (B) schematically show a state of the image detector mounted on an image detector holder through rubber cushions. FIGS. 2 (A) and (B) are a plan view and a front view of a rubber cushion used in the embodiment.

Figure 3:
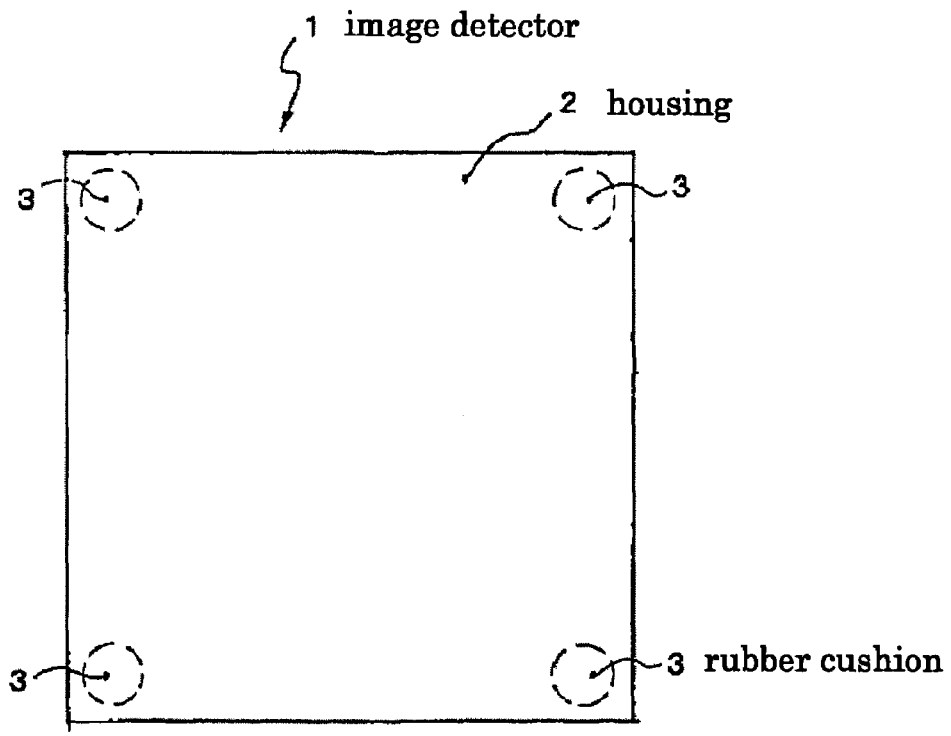
FIG. 3 Views schematically showing a housing configuration of a conventional image detector, and a state of the image detector mounted on an image detector holder using rubber cushions.
Figure 3:
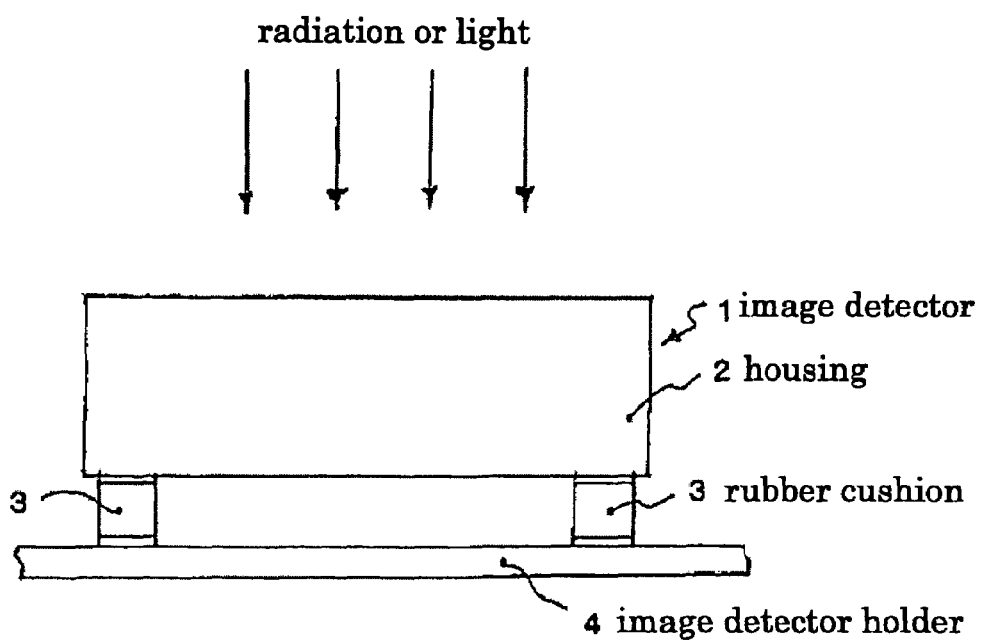
Figure 4:
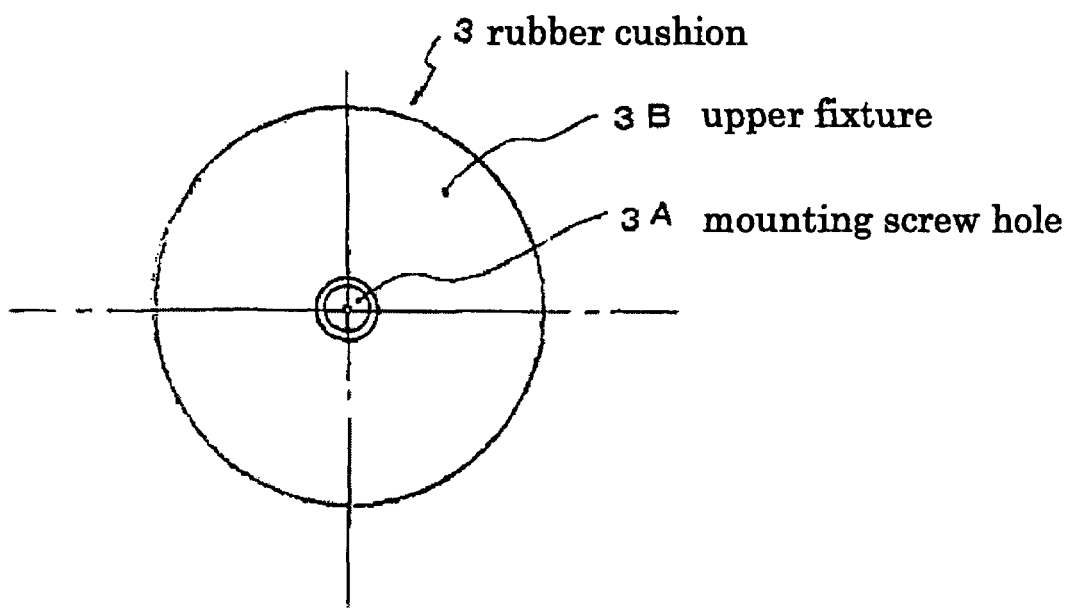
FIG. 4 Views showing a construction and configuration of a rubber cushion used in the prior art.
Figure 4:
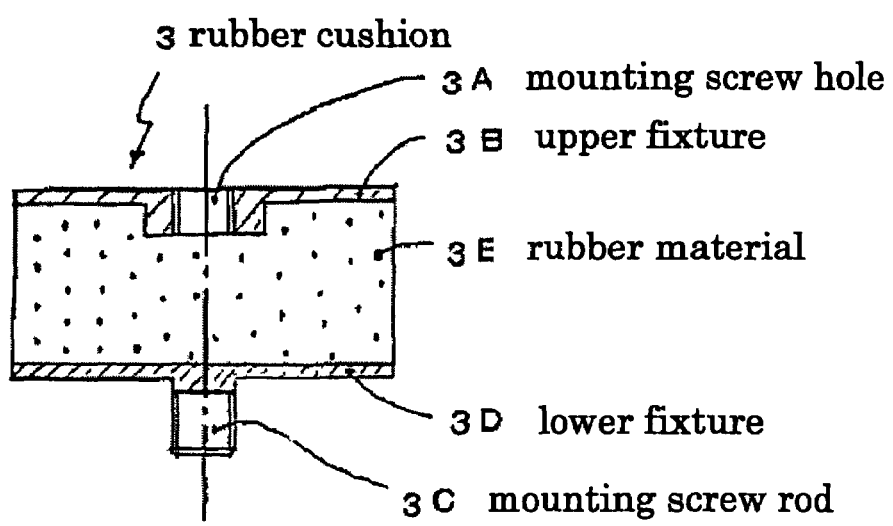

The housing 2 conventionally has a rectangular section as seen from FIG. 3 (B), but in this embodiment has a protrusive sectional shape as seen from FIG. 1 (B). Regarding the inner space of the housing 2 in this embodiment as divided into a housing central space 2A corresponding to the protrusion and two, right and left housing peripheral spaces 2B, the housing peripheral spaces 2B have shallower bottoms than the housing central space 2A.

A difference in thickness between the center and peripheries of the housing 2 is shorter than the length of cylindrical rubber cushions 3 used to attach the image detector 1 to an image detector holder 4. Each of the two rectangles at the peripheries shallower than the center has the shorter sides longer than the diameter of outer circles of the rubber cushions 3 used in this embodiment and shown in FIG. 2.

A required number of receptacles (not shown in FIG. 1), to which signal lines or power source lines wired inside the image detector 1 are connected, are arranged on or adjacent inner walls of two side faces between the bottoms of the housing peripheral spaces 2B and the bottom of the housing central space 2A, among the side faces of the housing 2. A required number of bores are formed in the above side faces, which have sizes necessary for fitting plugs 5, to which cables 6 of signal lines or power source lines wired outside the image detector 1 are connected, with the corresponding receptacles. These receptacles and plugs 5, which constitute connectors of signal lines and power source lines with the exterior of the image detector 1, are arranged in positions clear of the rubber cushions 3 attached to the housing 2 by a method described hereinafter. The length of the shorter sides of the bottoms of the housing peripheral spaces 2B and the length of the plugs 5 are determined so that contours of the connectors are included in the contour of the housing 2 as seen from the radiation or light incidence side.

The recitation in claim 2 "allow connectors of wires taken in from the exterior of said housing to be arranged not to protrude from a contour of said housing as seen from a radiation or light incidence side" means that, in the case of the above embodiment, for example, the plugs 5 have a shorter length than the short sides of the bottoms of the housing peripheral spaces 2B, so that the contours of the connectors, formed of the receptacles and plugs 5, of signal lines and power source lines with the exterior of the image detector 1 are arranged to be included in the contour of the housing 2 as seen from the radiation or light incidence side.

The image detector 1 with the housing 2 having the above configuration is mounted, with each of mounting holes formed in the four corners at the bottom being disposed on each of fixing screw holes 3A of the four rubber cushions 3 attached to the image detector holder 4, and is fixed on the four rubber cushions 3 with four screws. The four rubber cushions 3 are attached to the image detector holder 4 so that their outer circles do not protrude from the shallow bottoms of the peripheries of the housing 2.

As a result, the thickness of the image detector 1 including the rubber cushions 3, in the case of the image detector 1 with the housing 2 of conventional configuration, is a sum of the thickness of the housing 2 and the height of the rubber cushions 3, whereas in the case of the image detector 1 with the housing 2 of the configuration in this embodiment, it is a sum of the thickness of the peripheries of the housing 2 which is thinner than the center and the height of the rubber cushions 3. Where the thickness of the peripheries of the housing 2 which is thinner than the thickness of the housing 2 of conventional configuration, the thickness of the image detector 1 including the rubber cushions 3 becomes thinner than in the prior art.

The rubber cushions 3 used in this embodiment, as shown in FIG. 2, have the same structure as in the prior art, insofar as a rubber material 3E is held between an upper fixture 3B having a mounting screw hole 3A, and a lower fixture 3D having a mounting screw rod 3C. Each of the cylindrical upper fixture 3B and lower fixture 3D is cut away in portions thereof surrounded by two surfaces perpendicular to a mounting surface and parallel to each other, surfaces parallel to the mounting surface, and side faces of the cylinder. Thus, upper fixture cutout portions 3F and lower fixture cutout portions 3G are formed, respectively, with two parallel surfaces. The thickness of the cylindrical upper fixture 3B and lower fixture 3D and volume of the cutout portions are determined to be in such ranges that, even if these portions are cut out, both the upper fixture 3B and lower fixture 3D do not lose the strength required for anchoring the image detector 1.

The rubber cushions 3 as shown in FIG. 2 are used when attaching the image detector 1 to the image detector holder 4. When attaching the fixing screw rods 3C of the rubber cushions 3 to screw holes formed in the image detector holder 4, they can be tightened reliably with a tool such as a spanner, using the lower fixture cutout portions 3G. When screwing the image detector 1 to the mounting screw holes 3A of the rubber cushions 3 thereafter, screws can be turned while holding the upper fixture cutout portions 3F with a tool such as a spanner, for example. Since the upper fixtures 3B are prevented from rotating by friction with the screws, it is possible to prevent the rubber materials 3E being fixed in a twisted state.

In the above embodiment, the housing 2 having a protruding sectional shape has been described by way of example. Step portions may be formed in the four corners of the bottom of the housing 2 of rectangular parallelepiped to reduce the thickness of the housing 2, with one rubber cushion 3 attached to each such portion. In this case, the housing 2 has a larger volume than in the above embodiment. These portions can accommodate the connectors, formed of the receptacles and plugs 5, of signal lines and power source lines from the exterior of the image detector 1.

The recitation in claim 2 "allow connectors of wires taken in from the exterior of said housing to be arranged not to protrude from a contour of said housing as seen from a radiation or light incidence side" includes the case, as in the above embodiment, for example, of mounting, in the housing 2, the connectors, formed of the receptacles and plugs 5, of signal lines and power source lines from the exterior of the image detector 1.

INDUSTRIAL UTILITY

This invention relates to a two-dimensional image detector that can detect images of radiation or light, and a radiographic apparatus using the two-dimensional image detector.

The invention claimed is:

1. A two-dimensional image detector comprising, mounted in a housing, a planar image detecting substrate with a light receiving section having radiation or light detecting elements arranged in a matrix form, and parts necessary for outputting image information detected by the image detecting substrate to an exterior of the housing, characterized in that stepped portions are formed over an entire circumference or in a plurality of locations peripherally of a radiation or light non-incidence surface of the housing for reducing a thickness of the housing and attaching vibration proof members for holding said housing.

2. A two-dimensional image detector as defined in claim 1, characterized in that said stepped portions have outer surfaces thereof acting as portions for attaching the vibration proof members, and allow connectors of wires taken in from the exterior of said housing to be arranged not to protrude from a contour of said housing as seen from a radiation or light incidence side.

3. A radiographic apparatus characterized in that the two-dimensional image detector defined in claim 2 is mounted through the vibration proof members attached to said stepped portions.

4. A radiographic apparatus as defined in claim 3, characterized in that the vibration proof members are a rubber type.

5. A radiographic apparatus as defined in claim 4, characterized in that each of the rubber type vibration proof members includes a rubber material held between a pair of fixtures having mounting screws, at least one of said pair of fixtures having at least a set of two surfaces perpendicular to a mounting surface and parallel to each other.

6. A two-dimensional image detector as defined in claim 2, characterized in that the vibration proof members are a rubber type.

7. A radiographic apparatus characterized in that the two-dimensional image detector defined in claim 1 is mounted through the vibration proof members attached to said stepped portions.

8. A radiographic apparatus as defined in claim 7, characterized in that the vibration proof members are a rubber type.

9. A radiographic apparatus as defined in claim 8, characterized in that each of the rubber type vibration proof members includes a rubber material held between a pair of fixtures having mounting screws, at least one of said pair of fixtures having at least a set of two surfaces perpendicular to a mounting surface and parallel to each other.

10. A two-dimensional image detector as defined in claim 1, characterized in that the vibration proof members are a rubber type.

* * * * *